(12) United States Patent
Jessee et al.

(10) Patent No.: US 7,648,832 B2
(45) Date of Patent: *Jan. 19, 2010

(54) METHODS FOR LYOPHILIZING COMPETENT CELLS

(75) Inventors: Joel A. Jessee, Mount Airy, MD (US); Fredric R. Bloom, Germantown, MD (US); Thuan Trinh, Gaithersburg, MD (US)

(73) Assignee: Life Technologies, Corp., Carlsbad, CA (US)

( * ) Notice: Subject to any disclaimer, the term of this patent is extended or adjusted under 35 U.S.C. 154(b) by 121 days.

This patent is subject to a terminal disclaimer.

(21) Appl. No.: 11/214,800

(22) Filed: Aug. 31, 2005

(65) Prior Publication Data

US 2006/0014255 A1  Jan. 19, 2006

Related U.S. Application Data

(63) Continuation of application No. 10/120,163, filed on Apr. 11, 2002, now Pat. No. 6,960,464, which is a continuation of application No. 09/020,911, filed on Feb. 9, 1998, now abandoned.

(60) Provisional application No. 60/039,720, filed on Feb. 12, 1997.

(51) Int. Cl.
 *C12N 1/20* (2006.01)
 *A01N 63/00* (2006.01)

(52) U.S. Cl. ............... 435/260; 435/252.1; 435/252.2; 435/849; 424/93.4; 424/93.48

(58) Field of Classification Search .................. 435/260
 See application file for complete search history.

(56) References Cited

U.S. PATENT DOCUMENTS

| | | | |
|---|---|---|---|
| 3,843,453 A | 10/1974 | Freake | 195/103.5 |
| 4,038,143 A | 7/1977 | Juni | 195/100 |
| 4,446,230 A | 5/1984 | Zubrzycki | 435/6 |
| 4,520,019 A | 5/1985 | Ribi et al. | 424/195.1 |
| 4,681,852 A | 7/1987 | Tribe | 435/108 |
| 4,808,404 A | 2/1989 | Bhogal | 424/88 |
| 4,824,938 A | 4/1989 | Koyama et al. | 530/351 |
| 4,851,348 A | 7/1989 | Hanahan | 435/252.33 |
| 4,891,319 A | 1/1990 | Roser | 435/188 |
| 4,950,609 A | 8/1990 | Tischer et al. | 435/18 |
| 4,981,797 A | 1/1991 | Jessee et al. | 435/172.3 |
| 5,043,261 A | 8/1991 | Goodrich et al. | |
| 5,045,446 A | 9/1991 | Goodrich, Jr. et al. | 435/2 |
| 5,059,518 A | 10/1991 | Kortright et al. | 435/6 |
| 5,098,893 A | 3/1992 | Franks et al. | 514/54 |
| 5,149,656 A | 9/1992 | Bitton et al. | 435/288 |
| 5,153,004 A | 10/1992 | Goodrich, Jr. et al. | 424/533 |
| 5,178,884 A | 1/1993 | Goodrich et al. | 424/533 |
| 5,200,399 A | 4/1993 | Wettlaufer et al. | |
| 5,213,814 A | 5/1993 | Goodrich, Jr. et al. | 424/532 |
| 5,290,765 A | 3/1994 | Wettlaufer et al. | |
| 5,292,507 A | 3/1994 | Charley | 424/93 |
| 5,425,951 A | 6/1995 | Goodrich, Jr. et al. | 424/520 |
| 5,733,774 A | 3/1998 | Jin et al. | |
| 5,891,692 A | 4/1999 | Bloom et al. | 435/172.3 |
| 5,958,670 A | 9/1999 | Goodrich, Jr. et al. | 435/2 |
| 6,274,369 B1 | 8/2001 | Donahue, Jr. et al. | 435/252.33 |
| 6,383,810 B2 | 5/2002 | Fike et al. | 435/384 |
| 6,610,531 B1 | 8/2003 | Mateczun et al. | |
| 6,709,854 B2 | 3/2004 | Donahue, Jr. et al. | 435/252.33 |
| 6,855,494 B2 | 2/2005 | Bloom et al. | 435/6 |
| 6,872,357 B1 | 3/2005 | Bronshtein et al. | |
| 6,960,464 B2 | 11/2005 | Jessee et al. | |
| 2002/0081565 A1 | 6/2002 | Barnea et al. | |
| 2003/0044965 A1 | 3/2003 | Mateczun et al. | |
| 2004/0110267 A1 | 6/2004 | Sundar | |
| 2005/0053911 A1 | 3/2005 | Greener et al. | |
| 2005/0053991 A1 | 3/2005 | Greener et al. | |
| 2005/0074867 A1 | 4/2005 | Bronshtein et al. | |
| 2006/0014255 A1 | 1/2006 | Jessee et al. | |

FOREIGN PATENT DOCUMENTS

| | | |
|---|---|---|
| AU | A-27434/88 | 6/1989 |
| EP | 0 383 569 A2 | 8/1990 |
| EP | 0 508 496 A1 | 10/1992 |
| WO | WO 97/28248 | 8/1997 |
| WO | WO 97/36613 | 10/1997 |

OTHER PUBLICATIONS

American Type Culture Collection, *ATCC Bacteria and Bacteriophages*, 19th Ed., American Type Culture Collection, pp. 152-153, 161, 188, 277, 320 (1996).

Gherna, R.L., "Chapter 12. Preservation," in: *Manual of Methods for General Bacteriology*, Gerhardt, P., et al., eds., American Society for Microbiology, Washington, DC, pp. 208-217, (1981).

Herrmann, C.H. and Rice, A.P., "Specific Interaction of the Human Immunodeficiency Virus Tat Proteins with a Cellular Protein Kinase," *Virol.* 197:601-608, Academic Press, Inc., (1993).

Invitrogen Corporation Catalog, "Competent Cells," Invitrogen Corporation, pp. 71-72, (1992).

Leslie, S.B., et al., "Trehalose and Sucrose Protect Both Membranes and Proteins in Intact Bacteria during Drying," *Appl. Envir. Micro.* 61:3592-3597, American Society for Microbiology (1995).

Life Technologies, Inc., 1995-1996 Catalogue and Reference Guide, GIBCO BRL, pp. 16.2-16.12 (1995).

(Continued)

*Primary Examiner*—Vera Afremova

(57) ABSTRACT

This invention relates to a method for producing cells which are competent for transformation and which may be stably stored for extended periods of time at various temperatures. The method involves growing cells in a growth conducive medium, rendering said cells competent, and lyophilizing said competent cells. The invention further relates to competent cells produced by such a method, to methods of transforming said cells with a DNA molecule, and to a method of producing a desired protein or polypeptide from said transformed cells.

37 Claims, 9 Drawing Sheets

OTHER PUBLICATIONS

MacLachlan, P.R. and Sanderson, K.E., "Transformation of *Salmonella typhimurium* with Plasmid DNA: Differences Between Rough and Smooth Strains," *J. Bacter.* 161:442-445, American Society for Microbiology (1985).

Stratagene, "Competent Cells and Packaging Extracts," *Stratagene*, pp. 63-74, Stratagene (1995).

Co-Pending U.S. Appl. No. 09/606,314, Fike et al., filed Jun. 29, 2000.

Co-Pending U.S. Appl. No. 09/705,940, Fike et al., filed Nov. 6, 2000.

BioTeach, "advanced molecular biology laboratory," the Michael Smith Laboratories education facility, accessed online at http://bioteach.ubc.ca/ambl/expl.html, 3 pages.

Email exchange between Harry Yim, Ph.D. and Kenneth E. Sanderson, Ph.D., dated Dec. 14, 2004.

Lederberg, E.M. and Cohen, S.N., "Transformation of *Salmonella typhimurium* by Plasmid Deoxyribonucleic Acid," *J. Bacteriology* 119:1072-1074, American Society for Microbiology (1974).

Norgard, M.V., et al., "Factors Affecting the Transformation of *Escherichia coli* Strain $_x$1776 by pBR322 Plasmid DNA," *Gene* 3:279-292, Elsevier/North-Holland Biomedical Press (1978).

Roantree, R.J., et al., "The Effect of Defined Lipopolysaccharide Core Defects upon Antibiotic Resistance of *Salmonella typhimurium*," *J. Gen. Microbiol.* 103:223-234, Cambridge University Press (1977).

Sundquist, T. and Doers, M., "Technically Speaking. Optimized Cloning with T Vectors," *Promega Notes* 68:31-33, Promega Corporation (1998).

Wolfe, J. and Bryant, G., "Freezing, drying and/or vitrification of membrane-solute-water systems," *Cryobiology* 39:103-129, Academic Press (Sep. 1999).

Alexander, D.C., et al., "A simplified and efficient vector-primer cDNA cloning system," *Gene* 31:79-89, Elsevier Science Publishers (1984).

Bullock, W.O., et al., "XL1-Blue: A High Efficiency Plasmid Transforming recA *Escherichia coli* Strain With Beta-Galactosidase Selection," *BioTechniques* 5:376-378, Eaton Publishing Group (1987).

Cronan, Jr., J.E., "Thermal Regulation of the Membrane Lipid Composition of *Escherichia coli*," *J. Biol. Chem.* 250:7074-7077, the American Society of Biological Chemists, Inc. (1975).

de Mendoza, D., et al., "Overproduction of *cis*-Vaccenic Acid and Altered Temperature Control of Fatty Acid Synthesis in a Mutant of *Escherichia coli*," *J. Bacteriol.* 151:1608-1611, American Society for Microbiology (1982).

de Mendoza, D., et al., "Thermal Regulation of Membrane Fluidity in *Escherichia coli*," *J. Biol. Chem.* 258:2098-2101, the American Society of Biological Chemists, Inc. (1983).

de Mendoza, D. and J.E. Cronan, Jr., "Thermal regulation of membrane lipid fluidity in bacteria," *TIBS* 8:49-52, Elsevier Biomedical Press (1983).

Dente, L., et al., "pEMBL: a new family of single stranded plasmids," *Nucleic Acids Research* 11:1645-1655, IRL Press, Ltd. (1983).

Dityatkin, S.Ya. and B.N. Il'yashenko, "Acceptor properties of freeze-thawed bacteria in relation to isolated plasmid DNA," *Chem. Abs.* 89:295, Abstract No. 176192r, The American Chemical Society (1978).

Dityatkin, S.Ya. and B.N. Ilyashenko, "Frozen and thawed bacteria as recipients of isolated phage and plasmid DNA," *Chem. Abs.* 90:322, Abstract No. 183010d, The American Chemical Society (1979).

Dower, W.J., et al., "High efficiency transformation of *E. coli* by high voltage electroporation," *Nuc. Acids Res.* 16:6127-6145, IRL Press, Ltd. (1988).

Dutyatkin, S.Ya. and B.N. Il'yashenko, "Chromosomal transformation of frozen-thawed bacteria," *Chem. Abs.* 90:286-287, Abstract No. 148301c, The American Chemical Society (1979).

Gombos, Z., et al., "Unsaturation of fatty acids in membrane lipids enhances tolerance of the cyanobacterium *Synechocystis* PCC6803 to low-temperature photoinhibition," *Proc. Natl. Acad. Sci. USA* 89:9959-9963, National Academy of Sciences (1992).

Hanahan, D., "Techniques for Transformation of *E. coli*," in: *DNA cloning. vol. I. a practical approach.* Glover, D.M., ed., IRL Press Limited, Oxford, England, pp. 109-135 (1985).

Hanahan, D., et al., "Plasmid Transformation of *Escherichia coli* and Other Bacteria," *Meth. Enzym.* 204:63-113, Academic Press, Inc. (1991).

Hanahan, D. and F. R. Bloom, "Mechanisms of DNA Transformation," in: *Escherichia coli and Salmonella, Cellular and Molecular Biology,* 2nd Ed., vol. 2, Neidhardt, F.C., ed., ASM Press, pub., Washington, D.C., pp. 2449-2459 (Apr. 1996).

Inoue, H., et al., "High efficiency transformation of *Escherichia coli* with plasmids," *Gene* 96:23-28, Elsevier Science Publishers B.V. (1990).

Konev, S.V., et al., "Membrane-structural mechanism of the development of competence in *Escherichia coli* cells to calcium-dependent transfection by bacteriophage λ DNA," *Chem. Abs.* 89:295, Abstract No. 176191q, The American Chemical Society (1978).

Levinson, A., et al., "Minimal Size Plasmids Containing an M13 Origin for Production of Single-Strand Transducing Particles," *J. Mol. Appl. Gen.* 2:507-517, Raven Press (1984).

Lin, J.-J. and J. Kuo, "AFLP™: A Novel PCR-Based Assay for Plant and Bacterial DNA Fingerprinting," *Focus* 17:66-70, Life Technologies, Inc. (1995).

Liss, L.R., "New M13 Host: DH5αF' Competent Cells," *Focus* 9:13, Life Technologies, Inc. (1987).

Meselson, M. and R. Yuan, "DNA Restriction Enzyme from *E. coli*," *Nature* 217:1110-1114, Macmillan Publishers, Ltd. (1968).

Messing, J., "M13mp2 and Derivatives: A Molecular Cloning System for DNA Sequencing, Strand-Specific Hybridization, and in Vitro Mutagenesis," in *Recombinant DNA. Proceedings of the Third Cleveland Symposium on Macromolecules, Cleveland, Ohio,* Jun. 22-26, 1981, Walton, A.G., ed., Elsevier Scientific Publishing Co., Amsterdam, The Netherlands, pp. 143-153 (1981).

Morrison, D.A., "Transformation and Preservation of Competent Bacterial Cells by Freezing," *Meth. Enzym.* 68:326-331, Academic Press, Inc. (1979).

Neumann, E., et al., "Gene transfer into mouse lyoma cells by electroporation in high electric fields," *EMBO J.* 1:841-845, IRL Press, Ltd. (1982).

Newman, T., et al., "Cloning and Expression of the *ilvB* Gene of *Escherichia coli* K-12," *Mol. Gen. Gen.* 186:378-384, Springer-Verlag International (1982).

Norgard, M.V., et al., "Factors affecting the transformation of *Escherichia coli* strain $_x$1776 by pBR322 plasmid DNA," *Gene* 3:279-292, Elsevier/North-Holland Biomedical Press (1978).

Old, R.W. and S. B. Primrose, "Basic Techniques," in: *Principles of Gene Manipulation, An Introduction to Genetic Engineering,* Carr, N.G., ed., Blackwell Scientific Publications, pub., Oxford, England, pp. 6-21 (1994).

Pope, B. and H. M. Kent, "High efficiency 5 min transformation of *Escherichia coli*," *Nucleic Acids Res.* 24:536-537, Oxford University Press (Feb. 1996).

Potter, H., "Electroporation in Biology: Methods, Applications, and Instrumentation," *Anal. Biochem.* 174:361-373, Academic Press, Inc. (1988).

Reusch, R.N., et al., "Poly-β-Hydroxybutyrate Membrane Structure and Its Relationship to Genetic Transformability in *Escherichia coli*," *J. Bacteriol.* 168:553-562 American Society for Microbiology (1986).

Suzuki, M. and A.A. Szalay, "Bacterial Transformation Using Temperature-Sensitive Mutants Deficient in Peptidoglycan Synthesis," *Meth. Enzym.* 68:331-342, Academic Press, Inc. (1979).

Taketo, A., "Sensitivity of *Escherichia coli* to Viral Nucleic Acid. VIII. Idiosyncrasy of $Ca^{2+}$-dependent Competence for DNA," *J. Biochem.* 75:895-904. The Japanese Biomedical Society (1974).

Taketo, A., "$Ba^{2+}$-Induced Competence for Transfecting DNA," *Zeitschrift Für Naturforschung, Section c, Biosciences* 30c:520-522, Verlag Der Zeitschrift Für Naturforschung (1975).

Taketo, A., "Sensitivity of *Escherichia coli* to Viral Nucleic Acid, XII. $Ca^{2+}$- or $Ba^{2+}$-Facilitated Transfection of Cell Envelope Mutants," *Zeitschrift Für Naturforschung, Section c, Biosciences* 32c:429-433, Verlag Der Zeitschrift Für Naturforschung (1977).

Trinh, T., et al., "STBL2™: An *Escherichia coli* Strain for the Stable Propagation of Retroviral Clones and Direct Repeat Sequences," *Focus* 16:78-80, Life Technologies, Inc. (1994).

Tucker, W.T., et al., "Structural and Functional Analysis of the *par* Region of the pSC101 Plasmid," *Cell* 38:191-201, MIT Press (1984).

Ulrich, A.K., et al., "Genetic and Biochemical Analyses of *Escherichia coli* Mutants Altered in the Temperature-Dependent Regulation of Membrane Lipid Composition," *J. Bacteriol.* 154:221-230, American Society for Microbiology (1983).

van Die; I.M., et al., Transformation in *Escherichia coli*: Studies on the Role of the Heat Shock in Induction of Competence. *J. Gen. Microbio.* 129:663-670, Society for General Microbiology (1983).

Vieira, J. and J. Messing, "Production of Single-Stranded Plasmid DNA," *Meth. Enzym.* 153:3-11, Academic Press, Inc. (1987).

Wada, H., et al., "Contribution of membrane lipids to the ability of the photosynthetic machinery to tolerate temperature stress," *Proc. Natl. Acad. Sci. USA* 91:4273-4277, National Academy of Sciences (1994).

Yanisch-Perron, C., et al., "Improved M13 phage cloning vectors and host strains: nucleotide sequences of the M13mp18 and pUC19 vectors," *Gene* 33:103-119, Elsevier Science Publishers (1985).

Zagursky, R.J. and M.L. Berman, "Cloning vectors that yield high levels of single-stranded DNA for rapid DNA sequencing," *Gene* 27:183-191, Elsevier Science Publishers (1984).

Zimmerman, U. and J. Vienken, "Electric Field-Induced Cell-to-Cell Fusion," *J. Membrane Biol.* 67:165-182, Springer-Verlag (1982).

Anderson, D.M.W. and I.C.M. Dea, "Recent advances in the chemistry of *Acacia* gums," *J. Soc. Cosmet. Chem.* 22:61-76, Society of Cosmetic Chemists of Great Britain (1971).

Chung, C.T., et al., "One-step preparation of competent *Escherichia coli*: Transformation and storage of bacterial cells in the same solution," *Proc. Natl. Acad. Sci. USA* 86:2172-2175, National Academy of Sciences (1989).

Cohen, S.N., et al., "Nonchromosomal Antibiotic Resistance in Bacteria: Genetic Transformation of *Escherichia coli* by R-Factor DNA," *Proc. Natl. Acad. Sci. USA* 69:2110-2114, National Academy of Sciences (1972).

Cosloy, S.D. and M. Oishi, "Genetic Transformation in *Escherichia coli* K12," *Proc. Natl. Acad. Sci. USA* 70:84-87, National Academy of Sciences (1973).

Crowe, J.H., et al., "Stabilization of dry phospholipid bilayers and proteins by sugars," *Biochem. J.* 242:1-10, The Biochemical Society (1987).

Dagert, M. and S.D. Ehrlich, "Prolonged Incubation in Calcium Chloride Improves the Competence of *Escherichia coli* Cells," *Gene* 6:23-28, Elsevier/North-Holland Biomedical Press (1979).

*Grant & Hackh's chemical dictionary*, Grant, R.L., ed., McGraw-Hill, Inc., pp. 246, 346 (1987).

Green, J.L. and C.A. Angell, "Phase Relations and Vitrification in Saccharide-Water Solutions and the Trehalose Anomaly," *J. Phys. Chem.* 93:2880-2882, the American Chemical Society (1989).

Hanahan, D., "Studies on Transformation of *Escherichia coli* with Plasmids," *J. Mol. Biol.* 166:557-580, Academic Press, Inc. (1983).

Hatley, R.H.M., et al., "The Stabilization of Labile Biochemicals by Undercooling," *Process Biochem.* 22:169-172. Morgan-Grampain (1987).

Hatley, R.H.M. and F. Franks, "Variation in Apparent Enzyme Activity in Two-Enzyme Assay Systems: Phosphoenolpyruvate Carboxylase and Malate Dehydrogenase," *Biotechnol. & Appl. Biochem.* 11:367-370, Academic Press, Inc. (1989).

Heckly, R.J. and J. Quay, "A Brief Review of Lyophilization Damage and Repair in Bacterial Preparations," *Cryobiology* 18:592-597, Academic Press, Inc. (1981).

Kushner, S.R., "An Improved Method for Transformation of *Escherichia Coli* with ColE1 Derived Plasmids," In: *Genetic Engineering*, Boyer, H.W., and S. Nicosia, eds., Elsevier/North-Holland Biomedical Press, New York, NY, pp. 17-23 (1978).

Liu, H. and A. Rashidbaigi, "Comparison of Various Competent Cell Preparation Methods for High Efficiency DNA Transformation," *BioTechniques* 8:21-25, Eaton Publishing Group (1990).

Mandel, M. and A. Higa, "Calcium-dependent Bacteriophage DNA Infection," *J. Mol. Biol.* 53:159-162, Academic Press, Inc. (1970).

*Merck Index: An Encyclopedia of Chemicals, Drugs, and Biologicals*, 11th edition, Budavari, S. et al., eds., Merck & Co., Inc., Rahway, NJ, pub., p. 3 (1989).

Polisky, B., et al., "Specificity of substrate recognition by the *EcoRI* restriction endonuclease," *Proc. Natl. Acad. Sci. USA* 72:3310-3314, National Academy of Sciences (1975).

Sambrook, J. et al., "Plasmid Vectors: Preparation and Transformation of Competent *E. coli*," In: *Molecular Cloning: A Laboratory Manual, 2nd Ed.*, Cold Spring Harbor Laboratory Press, Cold Spring Harbor, New York, pp. 1.74-1.84 (1989).

Simione, Jr., F.P., "Key Issues Relating to the Genetic Stability and Preservation of Cells and Cell Banks," *J. Parenteral Sci. & Technol.* 46:226-232, Parenteral Science and Technology (1992).

Tang, X. et al., "The optimization of preparations of competent cells for transformation of *E. coli*," *Nucl. Acids Res.* 22:2857-2858, Oxford University Press (1994).

Weisburd, S., "Death-Defying Dehydration," *Science News* 133:107-110, Science Service (1988).

Life Technologies, Inc. 1993-94 Catalogue and Reference Guide, GIBCO BRL, pp. 6-10 and 9-4 (1993).

Laine, Marko J. et al., "Stable Transformation of the Gram-Positive Phytopathogenic Bacterium *Clavibacter michiganesis* subsp. sepedonicus with Several Cloning Vectors", *Applied and Environmental Microbiology* vol. 62, No. 5 May 1996, 1500-1506.

MacLachlan, P.R. et al., "Transformation of *Salmonella typhimurium* with Plasmid DNA: Differences Between Rough and Smooth Strains", *J. Bacteriol.* vol. 161, No. 1 1985, p. 442-445.

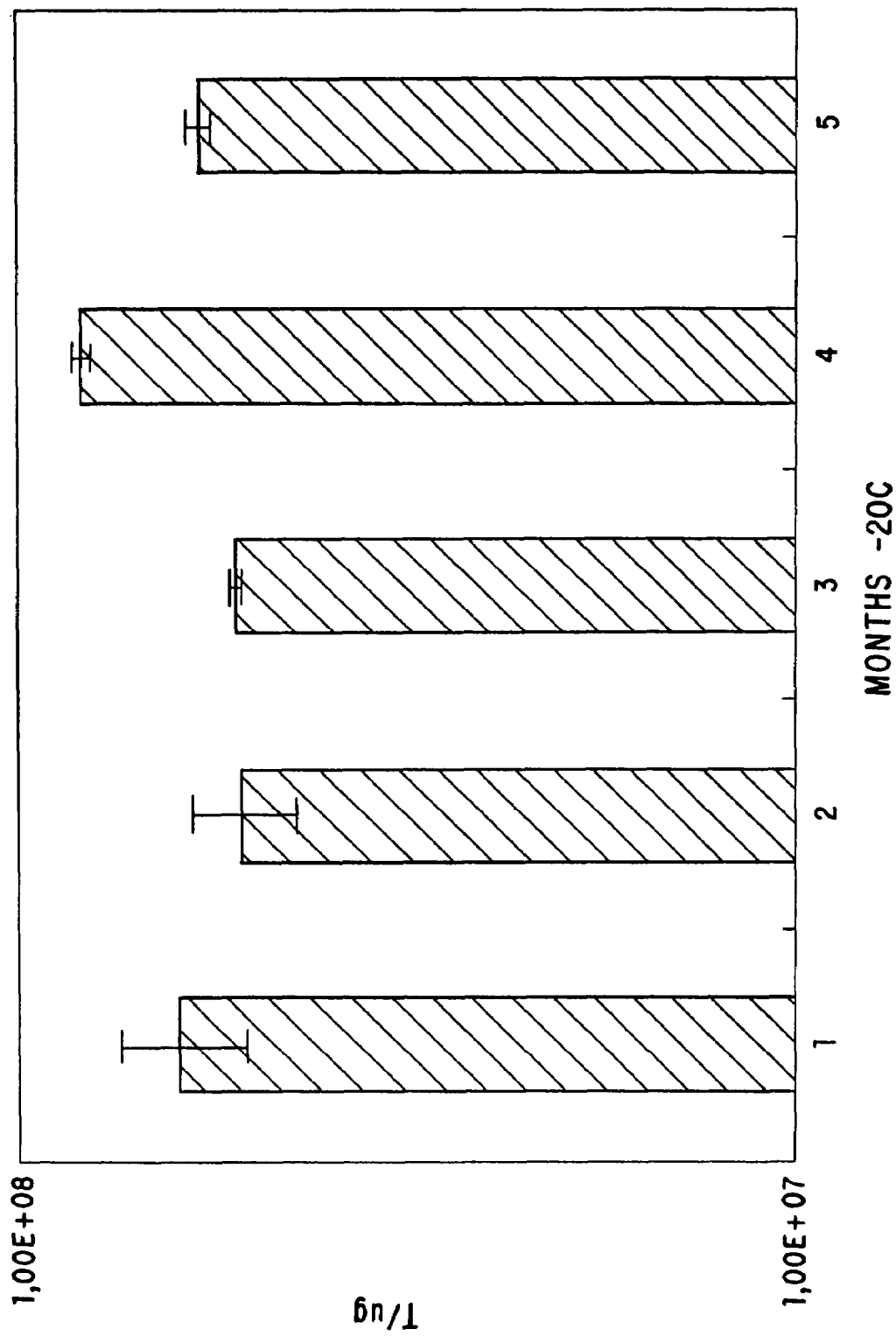

METHODS FOR LYOPHILIZING COMPETENT CELLS

CROSS-REFERENCE TO RELATED APPLICATIONS

This application is a continuation of U.S. patent application Ser. No. 10/120,163, filed Apr. 11, 2002, now U.S. Pat. No. 6,960,464 which is a continuation of U.S. application Ser. No. 09/020,911, filed Feb. 9, 1998, abandoned, which claims the benefit of U.S. provisional patent application No. 60/039,720, filed Feb. 12, 1997.

FIELD OF THE INVENTION

This invention relates to a method for producing cells which are competent for transformation and which may be stably stored for extended periods of time at various temperatures. The method involves growing cells in a growth conducive medium, rendering said cells competent, and lyophilizing said competent cells. The invention further relates to competent cells produced by such a method, to methods of transforming said cells with a DNA molecule, and to a method of producing a desired protein or polypeptide from said transformed cells.

BACKGROUND OF THE INVENTION

A number of procedures exist for the preparation of competent cells and the introduction of DNA into these cells. For example Mandel and Higa (*Journal of Molecular Biology* 53:159 (1970)) describe a procedure whereby bacteriophage DNA is combined with *E. coli* cells in the presence of 50 mM $Ca^{++}$ at 0° C., followed by a brief heat pulse at 37° C.-42° C. This method has been extended to the uptake of chromosomal DNA (Cosloy and Oishi, *Proceedings of the National Academy of Science* 70:84 (1973)) and plasmid DNA (Cohen et al., *Proc. Natl. Acad. Sci. USA* 69:2110 (1972)). A summary of the factors influencing the efficiency of transformation is given in Hanahan (*JMB* 166:557 (1983)). These factors include the addition of other cations such as Mg, Mn, or Rb to the Ca-treated cells as well as the prolonged incubation of the cells in $CaCl_2$. The efficiency of transformation of *E coli* cells is substantially enhanced by the Lu method described by Hanahan (JMB (1983), hereinafter referred to as "Hanahan C (1983)"). In the Hanahan (1983) method, the cells are grown at 37° C. in the presence of 20 mM Mg. Plasmid DNA is combined with the cells at 0° C. in the presence of Mn, Ca, Rb or K, dimethylsulfoxide (DMSO), dithiothreitol (DTT) and hexamine cobalt chloride. Competent cells of several strains of *Escherichia coli* (*E. coli*) prepared by the latter method have transformation efficiencies of from 1 to $5 \times 10^8$ transformants/μg plasmid DNA.

Another method for the preparation of competent *E. coli* cells is disclosed in U.S. Pat. No. 4,981,797 (Jessee and Bloom, 1991). That method includes the steps of growing the cells in a growth-conducive medium at a temperature of less than 37° C., rendering the cells competent and then freezing them.

Generally, frozen competent cells prepared by methods such as those summarized above have transformation efficiencies of about $1 \times 10^8$ transformants/1 g plasmid DNA These competent cells can be stored at -80° C. for several months without significant loss of transformation efficiency. However, cells prepared by the methods outlined above are extremely Unstable when stored at temperatures higher than -80° C. (e.g., -20° C.). Stable storage of competent cells at higher temperatures is highly desirable, since many research labs do not have access to -80° C. freezers.

SUMMARY OF THE INVENTION

The present invention relates to a method which allows competent cells to be lyophilized and stored for extended periods of time at various temperatures (-80° C. to room temperature) without appreciably losing transformation efficiency. Thus, the method of the invention provides competent cells which do not require specialized storage conditions (e.g., extremely low temperatures) to maintain the transformation efficiency of such cells.

The method of the invention comprises growing the cells in a growth conducive medium, rendering said cells competent, and lyophilizing said competent cells. According to the method of the invention, the cells are rendered competent by incubating the cells in a competence buffer, preferably at a low temperature (e.g., 0° C. to 4° C.). The cells are then lyophilized in the presence of a cryoprotectant.

The invention further relates to competent cells produced by such a method. In a preferred embodiment, the cells are *Escherichia* cells, most preferably *E. coli*. In a more preferred embodiment, the *E. coli* cells are selected from the group consisting of DH5α and DH10B.

In another embodiment, the invention relates to a method for transforming the lyophilized competent cells produced by the above-summarized method with a DNA molecule. The invention also relates to the transformed cell produced by this method.

In another embodiment, the invention relates to a method of producing a desired protein by first obtaining a lyophilized competent cell produced by the above method, transforming the lyophilized competent cell with a DNA molecule capable of expressing the desired protein, and then culturing the transformed cell under conditions sufficient to produced the desired protein. The invention also relates to a protein produced by this method.

BRIEF DESCRIPTION OF THE FIGURES

FIG. 4B is a graph showing the transformation efficiency of competent *E. coli* DH5α that had been lyophilized in NUNC cryovials, where the cells were first frozen in liquid nitrogen, lyophilized, and then stored at -20° C. for varying periods of time.

DETAILED DESCRIPTION OF THE PREFERRED EMBODIMENTS

Definitions

Figure 1:
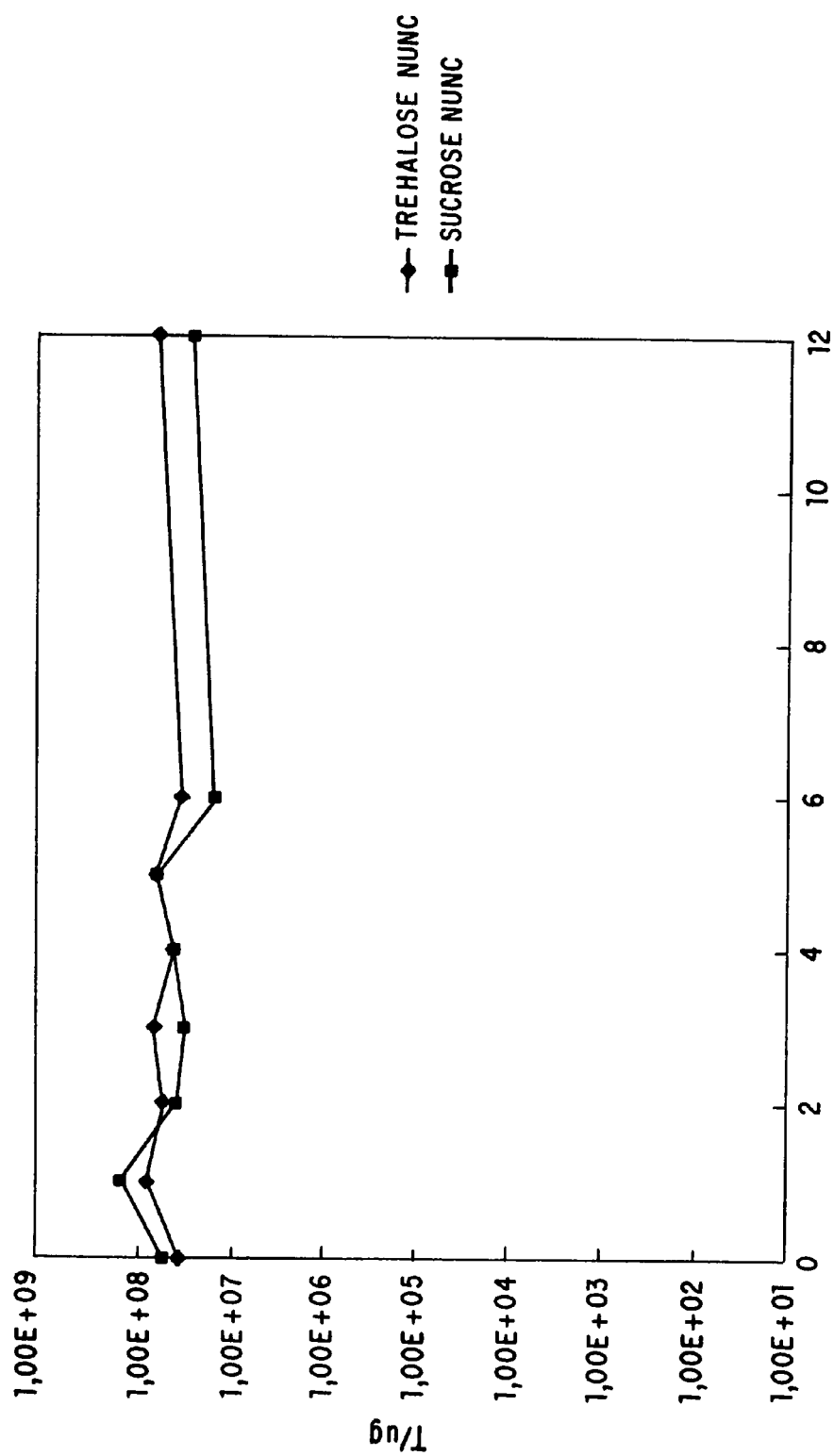
FIG. 1 is a graph showing the transformation efficiency of competent *E. coli* DH5α that had been lyophilized and stored at -20° C. in NUNC cryovials, where the cryoprotectant used was either trehalose or sucrose.

In the description that follows, a number of terms used in recombinant DNA technology are utilized extensively. In order to provide a clear and consistent understanding of the specification and claims, including the scope to be given such terms, the following definitions are provided.

DNA Molecule. Any DNA molecule, of any size, from any source, including DNA from viral, prokaryotic, and eukaryotic organisms. The DNA molecule may be in any form, including, but not limited to, linear or circular, and single or double stranded. Non-limiting examples of DNA molecules include plasmids, vectors, and expression vectors.

Cloning vector. A plasmid, phage DNA, a cosmid, or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression vector. A vector similar to a cloning vector but which is capable of expressing a gene which has been cloned into it, after transformation into a host. The cloned gene is usually placed under the control of (i.e., operably linked to) certain control sequences such as promoter sequences.

Stably stored. Within the meaning of the present invention, competent cells which can be "stably stored" are able to withstand storage for extended periods of time at a suitable temperature, without appreciably losing their transformation efficiency. By the term "without appreciably losing their transformation efficiency" is meant that the competent cells maintain about 40% to 100% preferably 60% to 100%, more preferably 70% to 100%, and most preferably about 80% to 100% of their original transformation efficiency (just after lyophilization) during a storage period of 30 days, preferably 60 days, more preferably 90 days, and most preferably 120 days, at a temperature of −20° C. Suitable storage temperatures vary from about room temperature to about −180° C. Preferably, the storage temperature ranges from about 4° C. to about −80° C., more preferably from about −20° C. to about −80° C. In a preferred aspect of the invention, the cells are stored at about −20° C. The storage period or time may range from about 0 days to about 150 days, preferably from about 240 days to about 365 days, and more preferably from about 365 days to about 450 days, although longer storage times may be used at temperatures of about −20° C. and below.

Competent cells. Cells having the ability to take up and establish an exogenous DNA molecule.

Substantially pure. As used herein means that the desired purified protein is free from contaminating cellular components which would be associated with the protein in nature. "Substantially pure" does not indicate that the protein must be completely free of all contaminants.

The method of the invention provides for the production of cells which are competent for transformation and which may be stably stored for extended periods at various temperatures. Both gram negative and gram positive prokaryotic cells (e.g., bacteria) can be used in accordance with the invention. Examples of suitable prokaryotic cells include, but are not limited to, *Escherichia* sp., *Klebsiella* sp., *Salmonella* sp., *Bacillus* sp., *Streptomyces* sp., *Streptococcus* sp., *Shigella* sp., *Staphylococcus* sp., and *Pseudomonas* sp. Non-limiting examples of species within each aforementioned genus that can be used in accordance with the invention include *Escherichia coli, Klebsiella pneumoniae, Bacillus subtilis, Salmonella typhimurium, Streptomyces aureus, Streptococcus mutans, Streptococcus pneumoniae*, and *Pseudomonas syringae*.

In a preferred embodiment, the cells which are rendered competent by the claimed method are *Escherichia*, most preferably *E. coli*. Non-limiting examples of *E. coli* strains which can be made competent by the claimed methods include DH5, DH5α, DH10, DH10B, HB101, RR1, JV30, DH11S, DM1, DH10B/p3, DH5αMCR, DH5α5'IQ, DH5α5', SCS1, Stab2, DH12S, DH5α-E, DH10BAC, XL1-Blue MRF, XL2-Blue MF, XL1-Blue MR, SURE Strain, SURE 2 Strain, XL1-Blue, XL2-Blue, AG1, JM101, JM109, JM110/SCS110, NM522, TOPP Strains, ABLE Strains, XL1-Red, BL21 Strains, TK BI Strain, and derivatives thereof. According to the method of the invention, the cells to be made competent are grown in a growth conducive medium. Any medium capable of supporting growth of the cells to be made competent can be used. Examples of such media include but are not limited to Luria Broth, Luria Broth supplemented with 20 mM $MgCl_2$, 0.001% thiamine, and 0.2% glucose; SOB medium containing 0.001% PPG (recipe given below); and 15/10 medium (recipe given below). Other suitable media will be readily recognized by one of skill in the art.

The incubation temperatures for growing the cells may vary from about 10° to about 42° C. Preferably, the temperatures range from about 12° to about 37° C., more preferably from about 15° C. to about 32° C., and most preferably from about 20° to about 25° C. In a preferred aspect of the invention, the cells are grown at about 23° C.

As one of ordinary skill in the art will understand, growth conditions and culture age can affect both the viability and the transformation efficiency of cells following cryopreservation. Cells grown in shake flask culture are generally more resistant to the stress of freeze-drying than are static broth cultures. Furthermore, the age of a culture also effects the ability of the culture to survive freeze-drying. Generally, cells harvested in late log or early stationary growth exhibit the greatest resistance to freeze-drying.

Thus, in accordance with the present invention, the cells are grown in shake flasks, although other means of growth may be used including fermentators. Shake flasks used in the invention can be of any size and any type. Preferably, baffled 2.8 L liter shake flasks are used for this processing. Incubation times will vary according to the conditions used (temperature, medium, aeration, etc.) and the cell type. Aeration in flasks varies according to the rotation per minute (rpm) used, with higher rpms resulting in higher aeration. Flasks are typically shaken at 100-500 rpms, preferably 200-400 rpms, and most preferably 0.200-300 rpms, although one of ordinary skill in the art may determine other preferred ranges. Cells are typically grown for a time and under conditions sufficient to reach an optical density (OD) at 550 nm between 0.1 to 2.0. Preferably, the OD ranges from 0.1 to 1.0, more preferably from 0.3 to 0.8, more preferably from 0.5 to 0.8, even more preferably from 0.5 to 0.7, still more preferably from 0.6 to 0.8, and most preferably from 0.66 to 0.75.

After the cells have reached the desired OD, the cells may be collected for further processing. In accordance with the invention, if the desired OD is not reached or is exceeded, the cells can again be reinoculated and the growth process repeated until a culture of sufficient optical density is obtained.

After the cells are collected (by centrifugation, filtration, etc.), they may optionally be chilled (e.g., 0° to 4° C. for 5 minutes to 2 hours). Collection of the cells may be accomplished by centrifuging the cells to obtain a cell pellet. Collection may also be accomplished by concentrating the cells and then centrifuging the concentrated cultures to obtain a cell pellet. Methods of concentrating the cells include, but are not limited to, dewatering the culture, filtering, or subjecting the culture to size exclusion chromatography, e.g. using Centricon™ columns (Amicon Corp., Lexington, Mass.).

After the cells are collected, the cells are resuspended in a competence buffer. A competence buffer is any solution that enables cells to take up and establish exogenous DNA Non-limiting examples of competence buffers include 50 mM $CaCl_2$, 10 mM Tris/HCl (Maniatis, T. et al., *Molecular Cloning: A Laboratory Manual*, 2nd ed., Cold Spring Harbor, N.Y. (1989)); 0.1 M MOPS (pH 6.5), 50 mM $CaCl_2$, 10 mM $RbCl_2$, 23% V/V DMSO; CCMB80 buffer (10 mM potassium acetate pH 7.0, 80 mM $CaCl_2.H_2O$, 20 mM $MnCl_2.4H_2O$, 10 mM $MgCl_2.6H_2O$, 10% glycerol adjusted to pH 6.4 with 0.1 N HCl); TFB buffer (Liu et al., *Biotechniques* 8(1):23-25 (1990)); and χ1776 buffer (Maniatis, T. et al., Molecular Cloning: A Laboratory Manual (2nd ed., Cold Spring Harbor, N.Y. (1989)). Other suitable buffers are disclosed in Tang et al., *Nucl. Acids Res.* 22(14):2857-2858 (1994); Chung et al., *Proc. Natl. Acad. Sci. U.S.A.* 86:2172-2175 (1989); M. Dagert and S. D. Ehrlich, *Gene* 6: 23-28 (1974); Kushner, S. R., In: Genetic Engineering (H. W. Boyer and S. Nicosia, eds.) pp. 17-23, Elsevier/North Holland, Amsterdam (1978); Mandel and Higa, *J. Mol. Biol.* 53:159-162 (1970); U.S. Pat. No. 4,981,797 by Jessee; and Hanahan, D., *J. Mol. Biol.* 166:557-580 (1983).

The cells suspended in the competence buffer are incubated for a sufficient time and at a temperature sufficient to make the cells competent to DNA uptake. Preferably, the cells are incubated at low temperature (0 to 4° C.) for 0 to 3 hours, more preferably 5 min. to 1 hr., and most preferably 5 min. to 30 min. After the cells have been made competent, a cryoprotectant may be added directly to the cell suspension. Preferably, the cells are collected and then resuspended in a cryoprotectant. The concentration of the cryoprotectant will vary depending on the cell type, buffers used, the type of cryoprotectant and other factors. Optimal conditions can be determined by one skilled in the art without undue experimentation. Cryoprotectants provide protection of the cells during the freezing process by depressing the freezing point, minimizing the effect of solution changes external to the cell, penetrating the cell to protect against solute concentration effects, and/or shifting the optimum cooling rate to lower values (F. P. Simione, *Journal of Parenteral Science & Technology*, 46(6):226-232 (1992)). Of course, the cryoprotectant must not be toxic to the cells. Further information on the preservation of living cells by freeze drying may be found in Simione, 1992.

Any cryoprotectant and combination thereof may be used in accordance with the invention. As will be apparent, the type and amount used may vary depending on the cell type and conditions used. Cryoprotectants that can be used in the present invention include, but are not limited to, carbohydrates and carbohydrate derivatives such as trehalose, sucrose, lactose, maltose, mannitol, galactose, ribose, fructose, xylose, mannose, dextrose, glucose, and sorbitol, and polymers such as polyethyleneamine, polyvinylpyrrolidone (PVP), ficoll, etc. Other cryoprotectants which can be used in accordance with the invention, such as acacia gum, albumin, gelatin, and sugar alcohols, will be readily recognized by one skilled in the art.

After the cells have been mixed with the cryoprotectant, the cell suspension may be aliquoted into containers to be used for lyophilization and storage, such as chilled cryovials, e.g., NUNC tubes (Gibco BRL, Gaithersburg, Md., Cat. No. 366656), or glass vials (Wheaton, Millville, N.J.). Prior to lyophilization, the cells are frozen at about −20° C. to about −180° C., preferably at about −80° C. to about −180° C., most preferably about −80° C.

Methods of freezing a sample to a temperature from about −80° to about −180° C. are well known in the art. These include overnight storage (about 16 hours) of the vials which contain the cells in a −80° C. freezer, or immersion of the vials which contain the cells in dry ice, or in a low temperature bath, such as dry ice ethanol, or in a bath containing liquid nitrogen. Other such systems are disclosed in *The Chemist's Companion: A Handbook of Practical Data, Techniques, and References*, Gordon, A. J., et al., eds., John Wiley and Sons, NY (1972).

The cells are then lyophilized by techniques which are well known in the art. Lyophilization is a process by which ice and/or moisture is removed from frozen cells by sublimation under vacuum at low, subzero temperatures (e.g., −40° to −50° C.). Any residual moisture associated with the "dried" preparation is then removed by gradually raising the temperature, resulting in evaporation. Thus, according to the invention, lyophilization comprises subjecting frozen cells to a vacuum under conditions sufficient to substantially remove moisture and/or ice from said cells (also referred to herein as substantially dried cells). The substantially dried cells may then be stored at various temperatures (room temperature to about −180° C., preferably about 4° C. to about −80° C., more preferably about −20° C. to about −80° C., and most preferably about −20° C.).

One such process for lyophilizing cells comprises the steps of
 (a) loading a container containing frozen cells into a lyophilizer, the lyophilizer having a temperature of about −40° to about −50° C.;
 (b) subjecting the cells to a vacuum; and
 (c) substantially drying the cells.

Preferably, the vacuum is less than about 100 μm, and the cells are dried by:
 (i) holding the temperature of the chamber at about −45° C. for about 2 hours; and
 (ii) increasing the temperature of the chamber from about −45° C. to about 10° C. at the rate of about 0.10 to 1.0° C./hr (preferably, 0.50 to 0.8° C./hr, and most preferably 0.60 to 0.8° C./hr).

The cell container may then be sealed and stored for extended time at various temperatures.

The viable cell count of competent cells produced by the method of the invention will remain at greater than about $1 \times 10^7$ cells/ml, preferably greater than about $1 \times 10^8$ cells/ml, and more preferably greater than about $1 \times 10^9$ cells/ml when stored at −20° C. for any time period from about 0 days to about 450 days, preferably from about 240 days to about 365 days, and more preferably from about 365 days to about 450 days. These cells will retain a transformation efficiency of at least about $1\times10^5$, preferably at least about $1\times10^6$, more preferably at least about $1\times10^7$, still more preferably at least about $1\times10'$ and most preferably at least about $1\times10^9$ transformants per microgram of DNA (T/μg). Suitable storage temperatures vary from about room temperature to about −180° C. Preferably, the storage temperature ranges from about 4° C. to about −80° C., more preferably from about −20° C. to about −80° C. In a preferred aspect of the invention, the cells are stored at about −20° C. The storage period or time may range from about 0 days to about 45 days, preferably from about 0 days to about 90 days, still more preferably from about 0 days to about 150 days, yet more preferably from about 240 days to about 365 days, and still more preferably from about 365 days to about 450 days, although longer storage times may be used at temperatures of about −20° C. and below. Competent cells produced by the method of the invention may be stored at −20° C. for at least one year while retaining substantially their transformation efficiency. Substantial retention of transformation efficiency means that after lyophilization, the cells will have a transformation efficiency after storage that is about 40% to 100%, preferably at about 60% to 100%, more preferably about 70% to 100% and most preferably about 80% to 100% of the transformation efficiency of the cells immediately after lyophilization.

The invention also pertains to transforming a lyophilized competent cell produced according to the method of invention. Transforming said lyophilized competent cells comprises obtaining a lyophilized competent cell, mixing said cell with a DNA molecule, and incubating said mixture under conditions sufficient to transform said cell with said DNA molecule. According to this aspect of the invention, the lyophilized competent cell may be any gram positive or gram negative bacteria including, but not limited to, *Escherichia*, *Klebsiella*, *Salmonella*, *Bacillus*, *Streptomyces*, *Streptococcus*, and *Pseudomonas*. Preferably, gram negative prokaryotic cells are transformed according to the method of the invention, more preferably *Escherichia*, and most preferably *E. coli*. According to the invention, any DNA molecule (e.g. vectors, plasmids, phagemids, expression vectors, etc.) may be used. Preferably, the cells are mixed with the DNA molecule in the presence of a competence buffer. According to the invention, the competence buffer may be added to the lyophilized competent cells prior to adding the DNA molecule or the DNA molecule and competence buffer may be added simultaneously to the lyophilized competent cells. Although mixing of the lyophilized competent cell with the DNA molecule and a competence buffer is preferred, any solution may be used to rehydrate and mix the competent cells with the DNA molecule. Such solutions include water, saline, or any suitable buffed.

After the cells have been transformed with the DNA molecule of interest, the transformed cells may be grown in a growth conducive medium. Typically, such a growth conducive medium contains an antibiotic to assist in selection of transformed cells. That is, the DNA molecule to be transformed may contain a selective marker (e.g. an antibiotic resistance gene), allowing selection of transformed cells when the corresponding antibiotic is used in the medium.

The invention also concerns a method of producing a desired protein by transforming a lyophilized competent cell with a DNA molecule encoding said desired protein. Thus, the invention concerns a method of producing a desired protein comprising obtaining a lyophilized competent cell produced according to the invention, transforming said cell with a DNA molecule capable of expressing said desired protein, and culturing said transformed cell under conditions sufficient to produce said desired protein. Cells which can be used according to this aspect of the invention including both gram negative and gram positive bacteria, preferably *Escherichia*, and most preferably *E. coli*. In this aspect of the invention, the cells are transformed by mixing the cells with a DNA molecule and incubating the mixture under conditions sufficient to transform said cell with said DNA molecule. This mixing step may be accomplished in any solution. Most preferably, the lyophilized competent cells are rehydrated in a competence buffer prior to adding the DNA molecule, or the lyophilized competent cells are simultaneously mixed with the DNA molecule and the competence buffer. Transformed cells may be selected according to techniques well known in the art including, for example, selection for marker genes on the DNA molecule (e.g. antibiotic resistance genes). After the transformed cell has been selected, the cell may then be cultured according to well known techniques in a growth conducive medium. Upon culturing the cell under appropriate conditions, the cell is capable of producing the desired protein. The desired protein may then be isolated, and a substantially pure protein obtained by well known protein purification techniques. Having generally described the invention, the same will be more readily understood by reference to the following examples, which are provided by way of illustration and are not intended to be limiting.

EXAMPLES

Example 1

A seed stock of *E. coli* DH5α cells (Gibco BRL, Gaithersburg, Md.) was prepared as follows: DH5α cells were streaked on an LB plate (32 g Gibco BRL LB agar (Life Technologies, Inc., Gaithersburg, Md.) per liter distilled water) and the plate was incubated for 36 hours at 23° C. Several colonies were picked into a 500 ml non-baffled shake flask containing 25 ml SOB medium (2% Bacto tryptone, 0.5% Bacto yeast extract 10 mM/NaCl, 2.5 mM KCl, 10 mM $MgCl_2$, 10 mM $MgSO_4$).

The flask was shaken at 23° C., 275 rpm, for several hours and the optical density at 550 nm is followed. When the optical density had reached 0.5, 10 ml of the cells were mixed with 10 ml of SOB:glycerol 60:40 (60 ml SOB, 40 ml glycerol, (Gibco BRL) in a 50 ml conical tube. The cells were mixed using a vortex mixer and were allowed to remain for 10 min. on ice. 1 ml aliquots were dispensed into NUNC cryovials (Catalog No. 366656) (Life Technologies, Inc., Gaithersburg, Md.) and were frozen in a dry ice ethanol bath for at least 5 minutes. The seeds were stored at −80° C.

A seed of DH5α cells stored at −80° C. was thawed on ice for 10 min. 0.450 ml of the thawed seed was inoculated into 1500 ml of SOB medium containing 0.001% PPG in a 2.8 L Fernbach flask. The flask was shaken at 23° C. (275 rpm). After approximately 20 hours, the culture had reached an optical density at 550 nm of 0.66. The cells were chilled on ice for 15 min. and collected by centrifugation using Corning 250 ml bottles with 250 ml of cell culture/bottle. The cells were centrifuged in a GS3 rotor at 4000 rpm 4° C. for 10 minutes in a Sorvall RC2B centrifuge.

Each cell pellet was resuspended in 75 ml of cold CCMB80 buffer (10 mM potassium acetate pH 7.0, 80 mM $CaCl_2.H_2O$, 20 mM $MnCl_2.4H_2O$, 10 mM $MgCl_2.6H_2O$, 10% glycerol adjusted to pH 6.4 with 0.1 N HCl). The cells were kept on ice for 20 min. The cell pellet was collected at 4° C. by centrifugation and each cell pellet was resuspended in 16 ml of either 9% aqueous trehalose (Quadrant, Cambridge England) or 12% aqueous sucrose. (Life Technologies Inc., Gaithersburg, Md.). 250 μl of the cell suspension was aliquoted into chilled 1.0 ml NUNC cryovials (Life Technologies, Inc., Gaithersburg, Md., Catalogue No. 366656). The caps were placed loosely on top of the vials and the vials were placed in a −80° C. freezer for 16 hours.

Alternatively, the cells were vialed in chilled 5 ml glass vials (Wheaton, Millville, N.J., Catalogue No. 223712). A rubber stopper was placed loosely on top of the vial, and the vial was placed in a −80° C. temperature for 16 hours.

After overnight storage in the −80° C. freezer, the vials were placed in a Hull lyophilizer and were subjected to vacuum drying according to the following protocol:
(a) Adjust shelf temperature to −45° C.
(b) Load frozen DH5α samples evenly on each shelf
(c) Close the chamber and turn on the vacuum system. When the vacuum is less than 100 m., start the drying program composed of the following 3 segments:
  i) Hold the shelf temperature at −45° C. for 2 hours.
  ii) Increase the shelf temperature from −45° C. to 10° C. at the rate of about 0.7° C./hour (55° C. in 72 hours).
(d) As soon as the shelf temperature reaches 10° C., the cells are moved to a 4° C. cold room.
(e) Store the vials at −20° C.

When the lyophilization cycle was complete, the cells were removed from the lyophilizer and taken to a 4° C. cold room where the caps were tightened. The cells were then placed in a foil pouch containing desiccant and the pouches were placed in a −20° C. freezer for storage.

To assay the cells for the transformation efficiency and viable cell count, the vials were removed from the −20° C. freezer and placed on wet ice for 6 minutes. The cells were rehydrated in 400 μl of a 1:1 mixture of CCMB80 buffer without glycerol (10 mM potassium acetate pH 7.0, 80 mM $CaCl_2.2H_2O$, 20 mM $MnCl_2.4H_2O$, 10 mM $MgCl_2.6H_2O$, adjusted to pH 6.4 with 0.1 N HCl) and FSB buffer (10 mM potassium acetate pH 7.0, 100 mM KCl, 45 mM $MnCl_2.4H_2O$, 10 mM $CaCl_2.2H_2O$, 3 mM hexaaminecobalt (III) chloride, 10% glycerol, 5% aqueous sucrose adjusted to pH 6.4 with 0.1 N HCl). 100 μl of the cells were removed from the vial and placed in a chilled Falcon™ 2059 tube (Becton Dickenson) for assay with 50 μg of pUC19 plasmid DNA. The viable cell count of the resuspended cells was also determined by standard dilution using 0.85% NaCl. The cells were then reassayed for transformation efficiency and viable cell count after storage at −20° C. The results of one such stability study is presented in FIGS. 1, 2 and 3.

Figure 2:
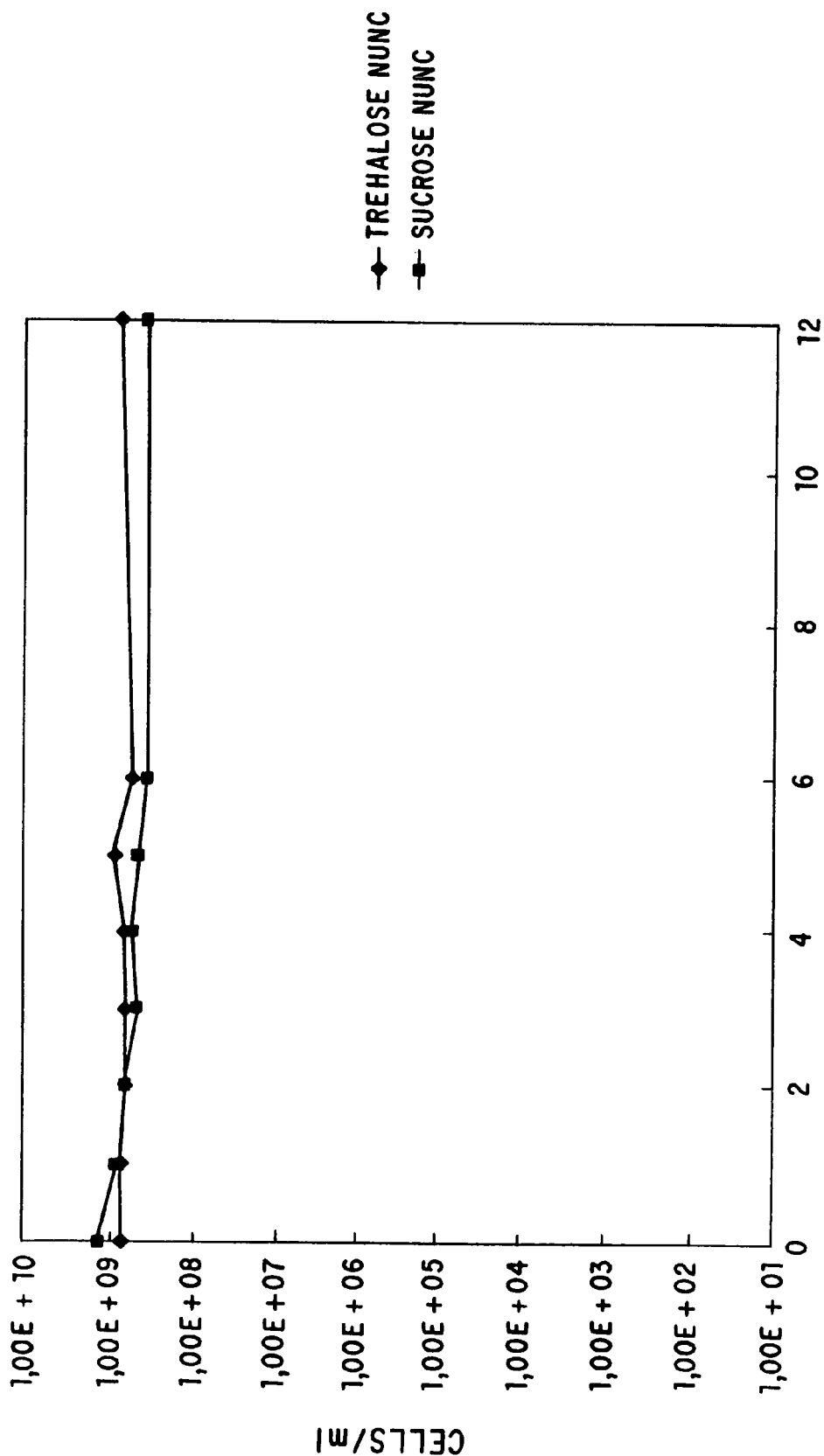
FIG. 2 is a graph showing the cell viability of competent *E. coli* DH5α that had been lyophilized and stored at -20° C. in NUNC cryovials, where the cryoprotectant used was either trehalose or sucrose.
Figure 3:
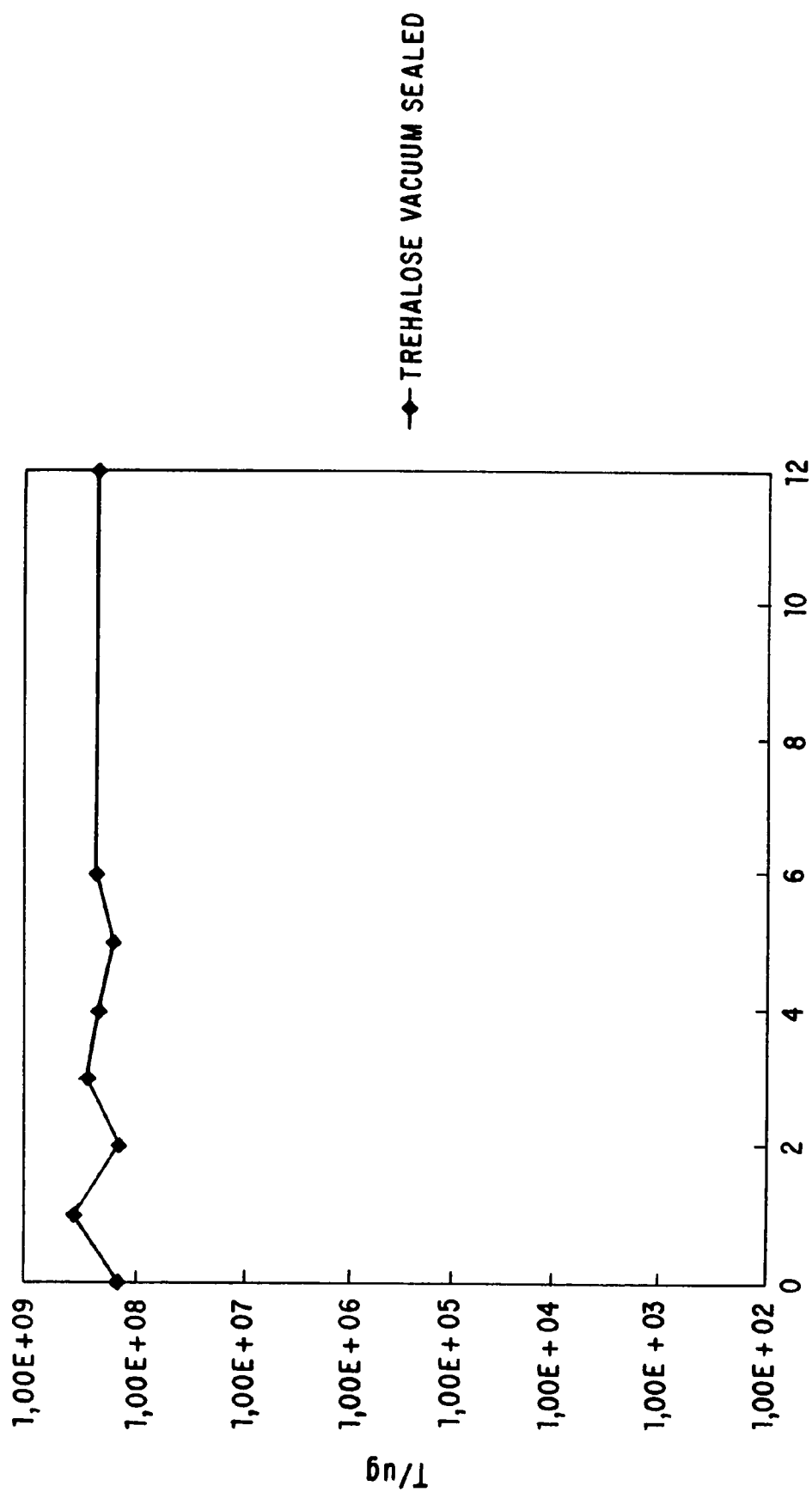
FIG. 3 is a graph showing the transformation efficiency of competent *E. coli* DH5α that had been lyophilized and stored at -20° C., where the cryoprotectant was trehalose, and the product was vacuum sealed in glass vials.

FIG. 1 indicates that DH5α cells lyophilized in NUNC cryovials using either sucrose or trehalose as the cryoprotectant retained a transformation efficiency of >$1.0×10^7$ T/μg when stored for at least 12 months at about −20° C. FIG. 2 indicates that the viable cell count of the cells stored in NUNC cryovials at about −20° C. remained at approximately $1.0×10^9$ cells/ml for at least 12 months. FIG. 3 indicates that the cells lyophilized using trehalose in glass vials which are vacuum sealed retain a transformation efficiency of >$1.0×10^8$ T/μg after storage at −20° C. for 12 months.

Example 2

The following example was carried out essentially as Example 1 with the following exceptions. The DH5×seed stored at −80° C. was thawed and 600 μl of the seed was inoculated into 1.7 L of SOB medium containing 0.001% PPG in a 2.8 L Fernbach flask. The flask was shaken for 18 hours at 23° C., 275 rpm. When the optical density at 550 nm had reached 0.194, 175 ml of the culture was inoculated into 1.7 L of SOB medium containing 0.001% PPG in a 2.8 L Fernbach flask. The flask was shaken for approximately 4 hours at 23° C., 275 rpm. When the optical density at 550 nm had reached 0.09, 2.7 ml of the culture was inoculated into 2 Fernbach flasks each containing 1.7 L SOB medium and 0.001% PPG. The flasks were shaken at 23° C., 275 rpm, for approximately 22 hours. When the optical density at 550 nm had reached between 0.648 and 0.722, the cultures were harvested and processed as in Example 1, with the exception that the cells were not chilled prior to collection by centrifugation. 200 ml of cells were then centrifuged at about 4° C. as described in Example 1 and the cell pellet was resuspended in 60 ml cold CCMB80 buffer. The cells were placed on ice for 20 minutes and again collected by centrifugation at about 4° C. The cell pellet was resuspended in 25.6 ml of cold 12% aqueous sucrose and the cells were placed on ice for 2 hours. 250 Vl of the cells were vialed after a 2 hour incubation on ice into chilled NUNC cryovials. The cells were frozen by placing the vials in a −80° C. freezer for 16 hours or were frozen by immersion in a liquid nitrogen bath. The cells were lyophilized as described in Example 1.

Figure 4A:
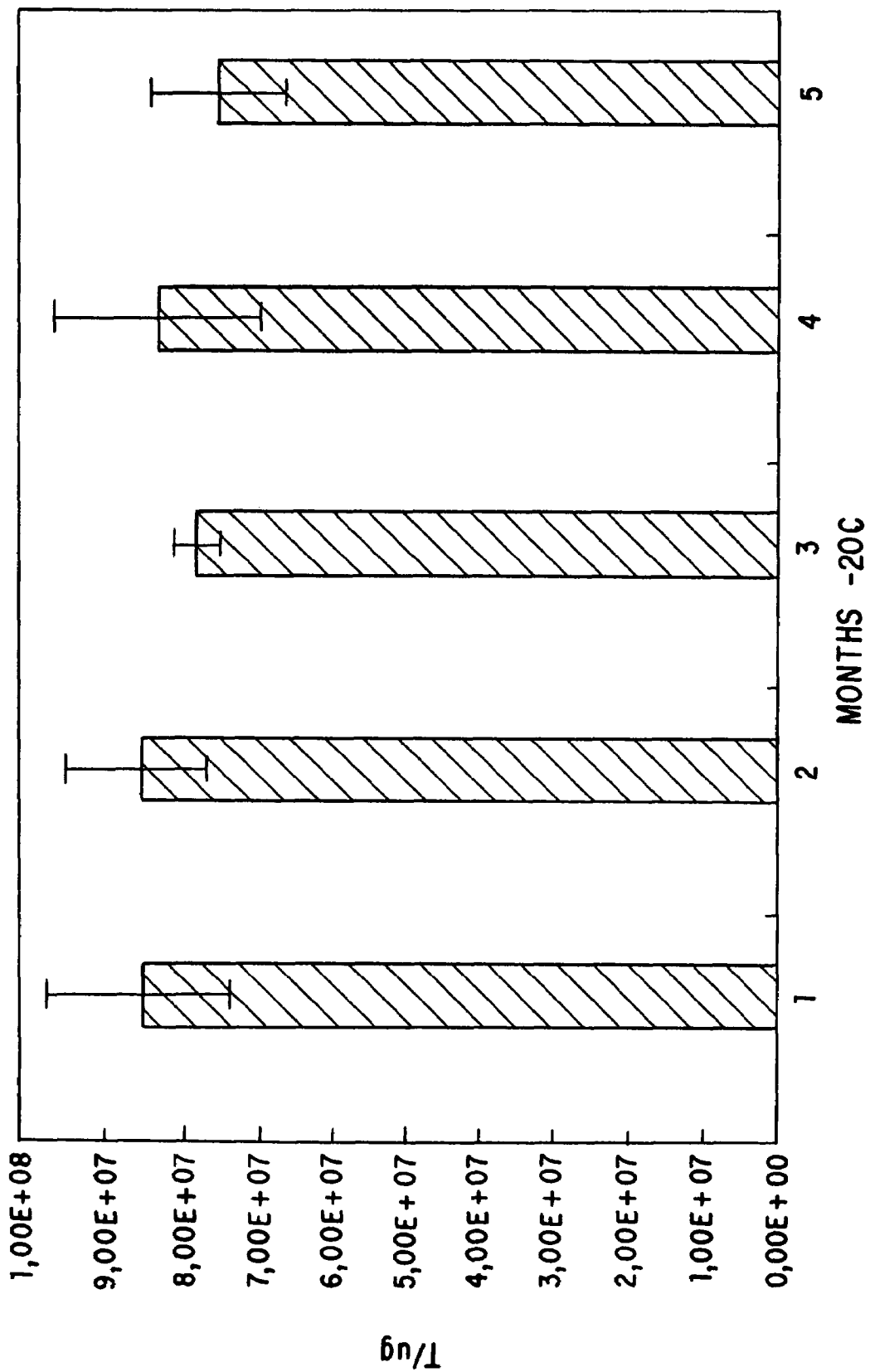
FIG. 4A is a graph showing the transformation efficiency of competent *E. coli* DH5α that had been lyophilized in NUNC cryovials, where the cells were first frozen at -80° C. for 16 hours, lyophilized, and then stored at -20° C. for varying periods of time.
Figure 5:
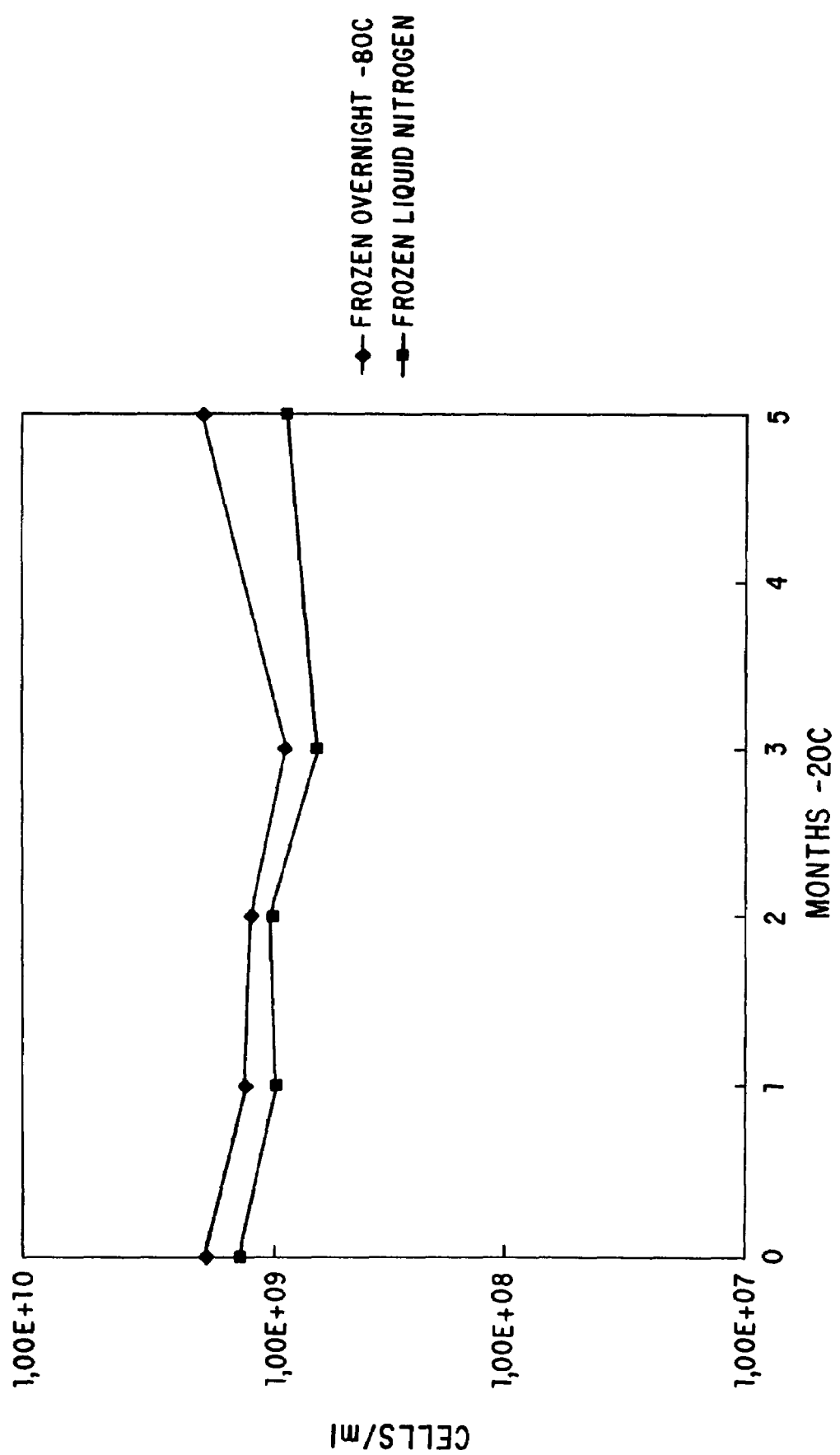
FIG. 5 is a graph showing the cell viability of competent *E. coli* DH5α that had been lyophilized in NUNC cryovials and stored at -20° C. for varying periods of time, where lyophilization and storage at −20° C. is preceded by either freezing at −80° C. for 16 hours, or freezing in liquid nitrogen.

The results are presented in FIGS. 4A, 4B, and 5. As seen in FIGS. 4A and 4B, the cells lyophilized in sucrose could be stored at −20° C. for at least 5 months without substantial loss of transformation efficiency. The transformation efficiency of the samples was at least $1×10^7$ T/μg. Samples frozen in either liquid nitrogen (FIG. 4B) or by storage at −80° C. for 16 hours (FIG. 4A) prior to lyophilization retained a transformation efficiency of >$1.0×10^7$ T/μg. As seen in FIG. 5, the lyophilized DH5α cells could be stored at −20° C. without significant loss of cell viability. Freezing in either liquid nitrogen or by storage at −80° C. for 16 hours prior to lyophilization resulted in stable storage of the cells. All samples had remained on ice for at least 2 hours before vialing. Therefore this data indicates that the cells may remain on ice in the cryoprotectant for at least 2 hours prior to freezing and lyophilization while substantially retaining transformation efficiency and cell viability.

Example 3

The following example was carried out essentially as in Example 2 with the following exceptions. Two DH5α seeds were thawed and 800 μl was inoculated into two 2.8 L Fernbach flasks, each containing 1.7 L of SOB medium and 0.001% PPG. The flasks were shaken at 23° C., 275 rpm, for approximately 19 hours. The optical density of the two flasks were 0.3918 and 0.3578, respectively. The cells were collected by centrifugation at 4° C. Each cell pellet was resuspended in 10 ml of room temperature SOB medium containing 0.001% PPG and were pooled (total of 120 ml). A 1:100 dilution of the cells had an optical density of 0.0754, indicating that the cell density was 7.54. Twenty ml of the cells were inoculated into 6 Fernbach flasks, each containing 1.7 L SOB medium and 0.001% PPG. The flasks were shaken at 23° C., 275 rpm, for 6.5 hours, at which time the optical densities of the flasks were 0.705, 0.783, 0.701, 0.749, 0.704, and 0.702. The flasks were chilled on ice for 15 minutes. Ten liters of the cells were concentrated in the 4° C. cold room by dewatering to 3 L in the following manner.

The peristaltic pump used was a Masterflex model 7529-30 (Cole Palmer) and the column used was a Microgon column # M22M-300-01N. The column was connected to the pump and rinsed once with 2 liters of autoclaved deionized water. The pump was turned on and 2 liters of 0.37% bleach was circulated through the system for 20 minutes. The system was then rinsed with 10 liters of autoclaved deionized water. 10 liters of the cell suspension was poured into the reservoir. The cell suspension was then circulated through the system with the pump speed set at 3.5 to reduce the volume to 3 liters. The process required approximately 25 minutes (approximately 280 ml/minute). The 3 liters of concentrated cell suspension was recovered from the reservoir by pumping the cell suspension out of the reservoir.

Six bottles each containing 250 ml of the concentrated cell suspension were centrifuged in a GS3 rotor at 4000 rpm for 10 minutes at 4° C. Each cell pellet was resuspended in 250 ml of cold CCMB80 buffer. The cells remained on ice for 20 minutes, and the cells were then collected by centrifugation at 4° C. Each cell pellet was resuspended in 53 ml of cold 9% aqueous trehalose. The cells were placed on ice or 1 hour, and 250 µl of the cells were vialed in 1.0 ml cryovials (Wheaton, Millville, N.J.). The vials were placed in a −80° C. freezer and remained for 16 hours before lyophilization. The cells were lyophilized in a Tri-Philizer™ model TR1585 lyophilizer (FTS Systems Inc.) with the temperature being increased at a rate of 0.6° C./hr.

Figure 6:
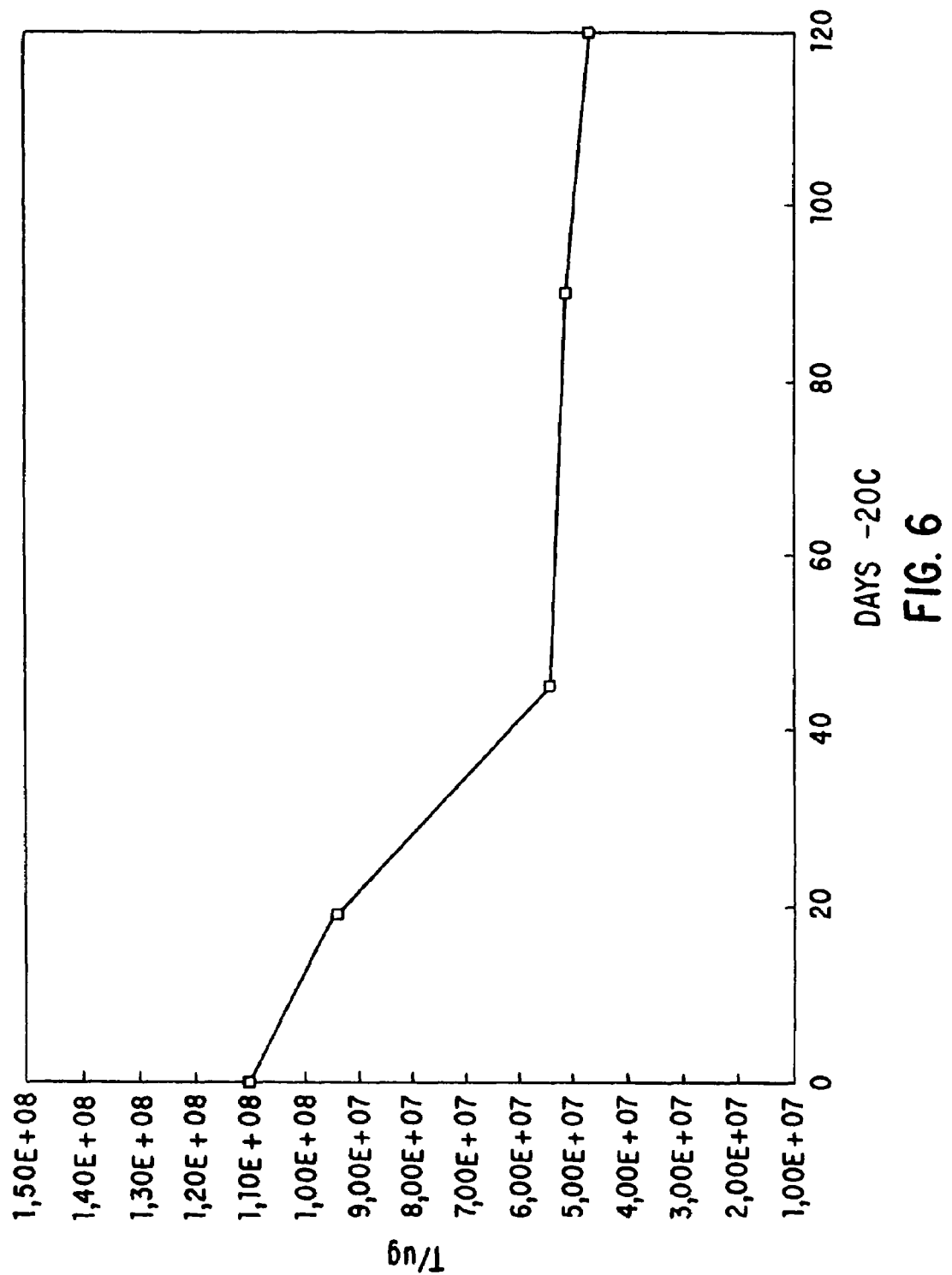
FIG. 6 is a graph showing transformation efficiency of competent *E. coli* DH5α that had been lyophilized according to Example 3.
Figure 7:
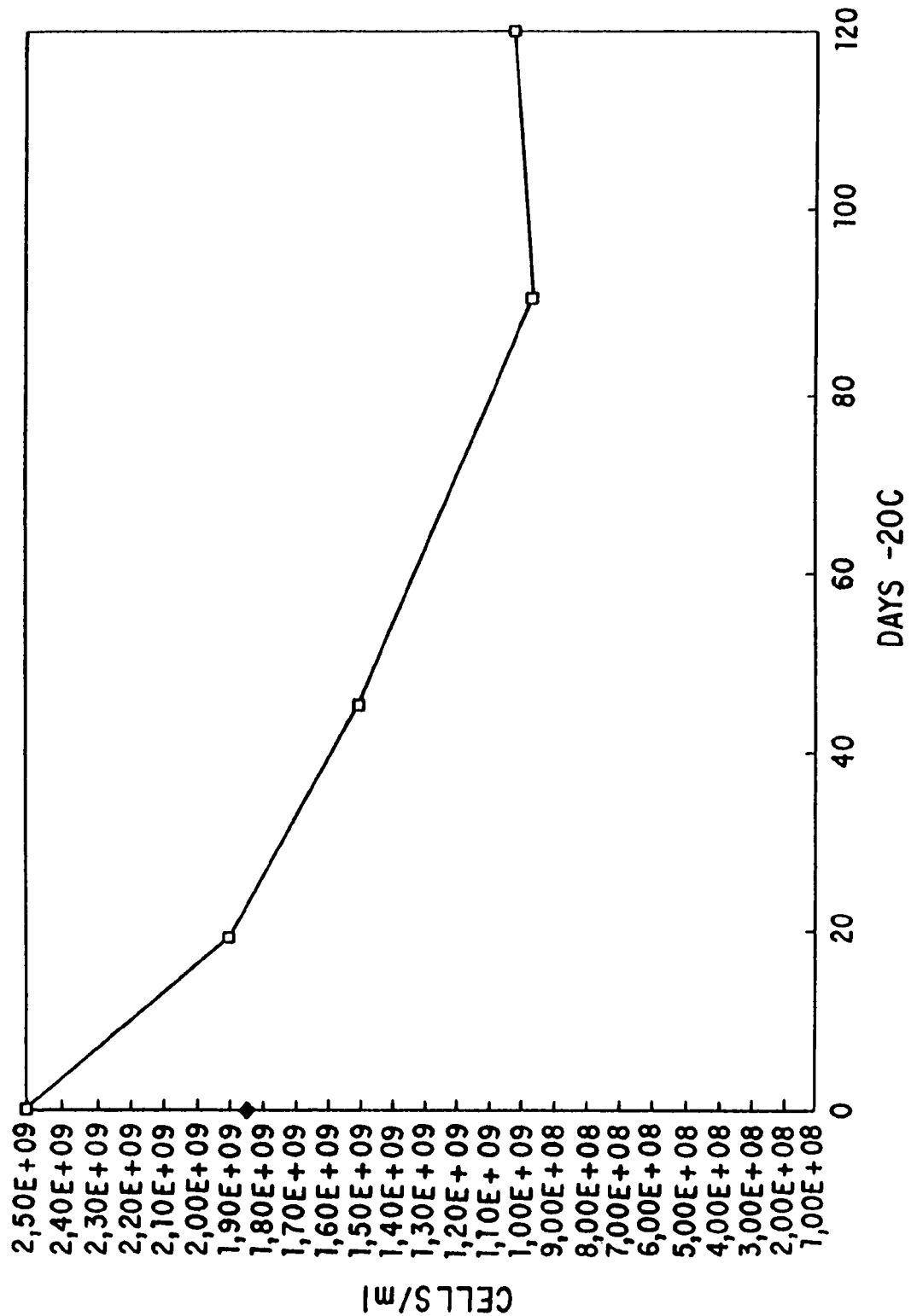
FIG. 7 is a graph showing the cell viability of competent *E. coli* DH5α that had been lyophilized according to Example 3.

The results are presented in FIGS. 6 and 7. FIG. 6 indicates that the cells can be stored at −20° C. for at least 4 months and maintain a transformation efficiency greater than $1 \times 10^7$ T/µg. FIG. 7 indicates that the cell viability remains at greater than $1 \times 10^9$ cells/ml after storage for 4 months at −20° C.

Example 4

This Example was performed essentially as Example 1 with the following exceptions. *E. coli* strain DH10B was streaked from a master seed stored at −80° C. onto an LB plate containing 100-µg/ml streptomycin. The plate was incubated for 24 hours at 23° C. A single colony was picked from the plate and inoculated into a flask containing 250 ml of 15/10 medium (1.0% Bacto tryptone, 1.5% Bacto yeast extract, 10 mM NaCl, 2 mM KCl, 10 mM $MgCl_2$, 10 mM $MgSO_4$, 0.001% polypropylene glycol (PPG)). The flask was shaken at 23° C., 260 rpm in a New Brunswick Psycrotherm™ shaker for 16 hours. Six ml of the culture was inoculated into a 2.8 L Fernbach flask containing 1.25 L of 15/10 medium, and the flask was shaken at 23° C., 260 rpm. The optical density at 550 nm was initially 0.1. The flask was shaken until the optical density was 0.7, and the cells were then collected by centrifugation at 4° C. The cells were processed as in Example 1. After resuspension in the cryoprotectant, 1 ml of the cell suspension was aliquoted into sterile 5 ml glass vials (Wheaton) and the cells were frozen for 5 minutes in a dry ice ethanol bath. Rubber stoppers were fitted loosely on the vials and the vials were placed in the lyophilizer. The cells were lyophilized according to the program described in Example 1 except that the vials were sealed under vacuum.

Figure 8:
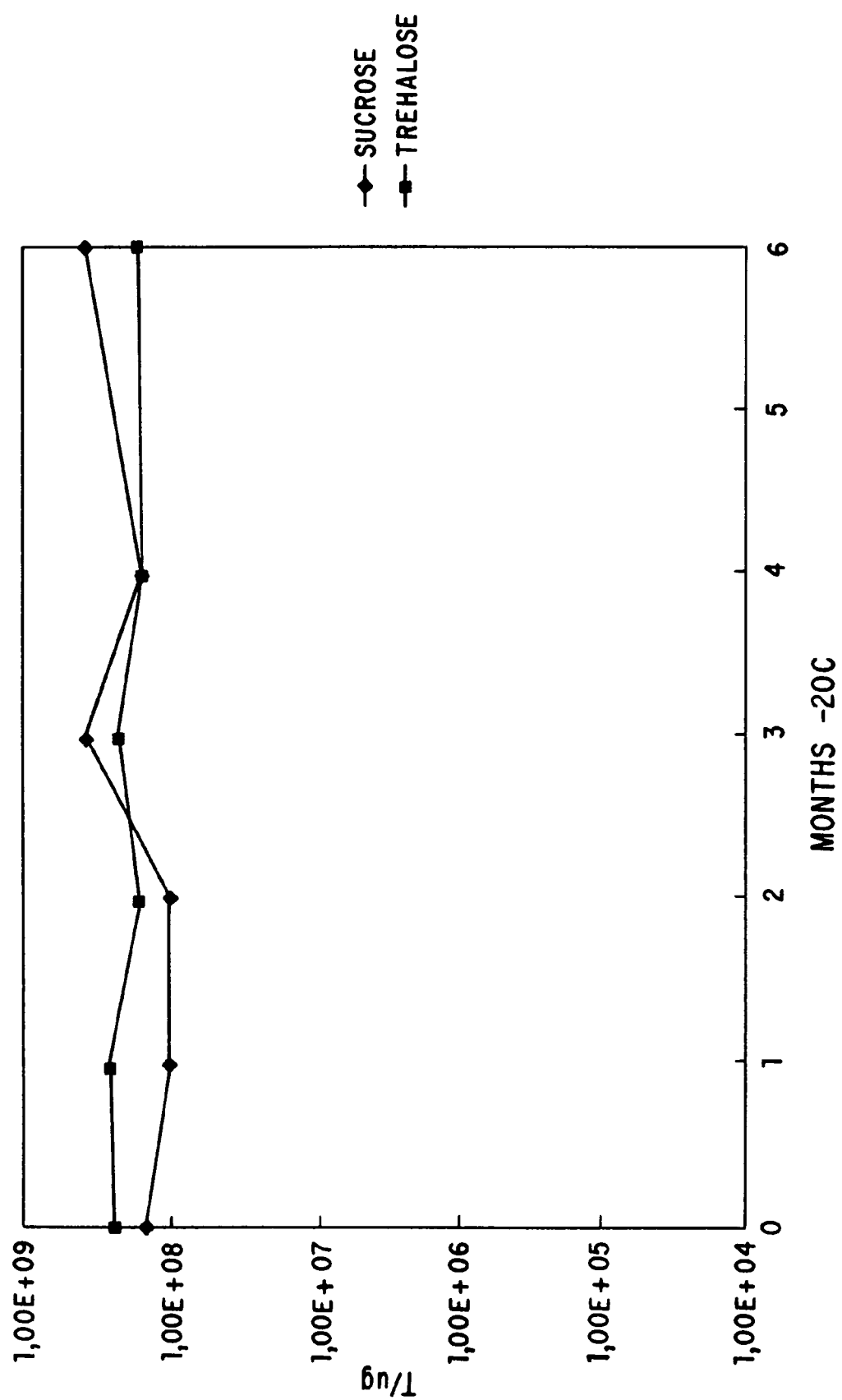
FIG. 8 is a graph showing the transformation efficiency of competent *E. coli* DH10B that had been lyophilized in glass vials which were vacuum sealed, and stored at −20° C., where the cryoprotectant used was either trehalose or sucrose.

After lyophilization, the vials were removed from the lyophilizer, and were stored at −20° C. in foil pouches containing desiccant. At intervals, vials were removed from the freezer and were assayed for transformation efficiency essentially as in Example 1, with the exception that the cells were resuspended in 2 ml of CCMB80 buffer without glycerol. The results are presented in FIG. 8. The data indicate that *E. coli* strain DH10B can be lyophilized and stored at −20° C. for at least 6 months while substantially retaining their transformation efficiency. Samples retain a transformation efficiency of >$1 \times 10^8$ T/µg after extended storage at −20° C.

It will be clear that the invention may be practiced otherwise than as particularly described in the foregoing description and Examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. A method of preparing lyophilized gram negative prokaryotic competent cells, comprising first rendering gram negative prokaryotic cells competent, then lyophilizing said competent cells, wherein said lyophilized competent cells exhibit a transformation efficiency of between about $1 \times 10^5$ and $1 \times 10^9$ transformants per microgram of DNA upon rehydration.

2. The method of claim 1, wherein said cells are selected from the group consisting of *Escherichia, Klebsiella, Salmonella* and *Pseudomonas*.

3. The method of claim 2, wherein said cells are *Escherichia* cells.

4. The method of claim 3, wherein said *Escherichia* cells are *E. coli* cells.

5. The method of claim 4, wherein said cells are selected from the group consisting of DH5, DH5α, DH10B, HB101, RR1, JV30, DH11S, DM1, DH10B/p3, DH5αMCR, DH5αF'IQ, DH5αF', SCS1, Stbl2, DH12S, DH5α-E, DH10BAC, XL-1Blue MRF, XL2-Blue MRF, XL1-Blue MR, SURE Strain, SURE 2 Strain, XL-1 Blue, XL2-Blue, AG1, JM101, JM109, JM110/SCS110, NM522, TOPP strains, ABLE Strains, SL1-Red, BL21 Strains, TK BI Strain and derivatives thereof.

6. The method of claim 1, wherein said cells have a transformation efficiency of about $1 \times 10^5$ transformants per microgram of DNA.

7. The method of claim 1, wherein said cells have a transformation efficiency of about $1 \times 10^6$ transformants per microgram of DNA.

8. The method of claim 1, wherein said cells have a transformation efficiency of about $1 \times 10^7$ transformants per microgram of DNA.

9. The method of claim 1, wherein said cells have a transformation efficiency of about $1 \times 10^8$ transformants per microgram of DNA.

10. The method of claim 1, wherein said cells have a transformation efficiency of about $1 \times 10^9$ transformants per microgram of DNA.

11. A method of preparing lyophilized gram negative prokaryotic competent cells, comprising first rendering gram negative prokaryotic cells competent, then lyophilizing said competent cells, wherein said lyophilized competent cells upon rehydration exhibit a transformation efficiency after storage for 30 days to 120 days at −20° C. that is about 40% to 100% of the transformation efficiency that said cells exhibit upon rehydration immediately after lyophilization.

12. The method of claim 11, wherein said cells are selected from the group consisting of *Escherichia, Klebsiella, Salmonella* and *Pseudomonas*.

13. The method of claim 12, wherein said cells are *Escherichia* cells.

14. The method of claim 13, wherein said *Escherichia* cells are *E. coli* cells.

15. The method of claim 14, wherein said cells are selected from the group consisting of DH5, DH5α, DH10B, HB101, RR1, JV30, DH11S, DM1, DH10B/p3, DH5αMCR, DH5αF'IQ, DH5αF', SCS1, Stbl2, DH12S, DH5α-E, DH10BAC, XL-1Blue MRF, XL2-Blue MRF, XL1-Blue MR, SURE Strain, SURE 2 Strain, XL-1 Blue, XL2-Blue, AG1, JM101, JM109, JM110/SCS110, NM522, TOPP strains, ABLE Strains, SL1-Red, BL21 Strains, TK Bi Strain and derivatives thereof.

16. The method of claim 11, wherein the transformation efficiency of said cells after storage for 30 days to 120 days at −20° C. is about 60% to 100% of the transformation efficiency of said cells immediately after lyophilization.

17. The method of claim 11, wherein the transformation efficiency of said cells after storage for 30 days to 120 days at −20° C. is about 70% to 100% of the transformation efficiency of said cells immediately after lyophilization.

18. The method of claim 11, wherein the transformation efficiency of said cells after storage for 30 days to 120 days at −20° C. is about 80% to 100% of the transformation efficiency of said cells immediately after lyophilization.

19. A method of preparing lyophilized competent cells, comprising (a) growing said cells in a growth conducive medium, (b) rendering the cells competent, and then (c) lyophilizing said competent cells, wherein said competent cells do not appreciably lose transformation efficiency when stored for extended periods of time.

20. The method of claim 19, wherein said competent cells are lyophilized in the presence of a cryoprotectant.

21. The method of claim 19, wherein said cells are rendered competent by incubating the cells in a competence buffer.

22. The method of claim 21, wherein said cells are incubated in a competence buffer at a temperature between 0° C. to 4° C.

23. The method of claim 19, wherein said cells are *E. coli*.

24. The method of claim 23, wherein said *E. coli* cells are selected from the group consisting of DH5α and DH10B.

25. The method of claim 19, wherein said lyophilized competent cells exhibit a transformation efficiency of between about $1\times10^5$ and $1\times10^9$ transformnants per microgram of DNA upon rehydration.

26. The method of claim 19, wherein said lyophilized competent cells upon rehydration and after storage for an extended period of time exhibit a transformation efficiency that is about 40% to 100% of the transformation efficiency of what said cells exhibit when rehydrated immediately after lyophilization without being subjected to storage for an extended period of time.

27. The method of claim 26, wherein said storage is for 30 days to 120 days.

28. The method of claim 26, wherein said storage is at −20° C.

29. A composition comprising:
a plurality of competent gram negative bacterial cells; and
at least one cryoprotectant;
wherein said composition is lyophilized, and wherein said competent gram negative bacterial cells, when rehydrated, exhibit a transformation efficiency of between about $10^5$ to about $10^9$ transformants/μg DNA.

30. The composition according to claim 29, wherein said competent gram negative bacterial cells are storage stable from room temperature to about −80° C.

31. The composition according to claim 29, wherein said competent gram negative bacterial cells are storage stable at −20° C.

32. The composition according to claim 29, wherein said competent gram negative bacterial cells are storage stable at −20° C. for at least 1 year.

33. The composition according to claim 29, wherein said cryoprotectant is selected from the list trehalose, sucrose, lactose, maltose, mannitol, galactose, ribose, fructose, xylose, mannose, dextrose, glucose, and sorbitol, polyethyleneamine, polyvinylpyrrolidone (PYP), ficoll, acacia gum, albumin, gelatin, and a sugar alcohol.

34. The composition according to claim 29, wherein said gram negative bacterial cells are selected from the group consisting of *Escherichia, Klebsiella, Salmonella* and *Pseudomonas*.

35. The composition according to claim 29, wherein said gram negative bacterial cells are *Escherichia* cells.

36. The method of claim 29, wherein said gram negative bacterial cells are *E. coli* cells.

37. The method of claim 29, wherein said gram negative bacterial cells are selected from the group consisting of DH5, DH5α, DH10B, HB101, RR1, JV30, DH11S, DM1, DH10B/p3, DH5αMCR, DH5αF"IQ, DH5αF', SCS1, Stbl2, DH12S, DH5α-E, DH10BAC, XL-1Blue MRF, XL2-Blue MRF, XL1-Blue MR, SURE Strain, SURE 2 Strain, XL-1 Blue, XL2- Blue, AG1, JM101, JM109, JM110/SCS110, NM522, TOPP strains, ABLE Strains, SL1-Red, BL21 Strains, TK Bi Strain and derivatives thereof.

* * * * *